United States Patent
Loddeke et al.

(10) Patent No.: US 6,527,552 B2
(45) Date of Patent: Mar. 4, 2003

(54) LUBRICATED DISPOSABLE PROPHYLAXIS ANGLE

(75) Inventors: Gerald R. Loddeke, O'Fallon, MO (US); Brendan J. McCrea, Manchester, MO (US)

(73) Assignee: Young Dental Manufacturing I, L.L.C., Earth City, MO (US)

( * ) Notice: Subject to any disclaimer, the term of this patent is extended or adjusted under 35 U.S.C. 154(b) by 0 days.

(21) Appl. No.: 09/880,326

(22) Filed: Jun. 13, 2001

(65) Prior Publication Data

US 2002/0192618 A1 Dec. 19, 2002

(51) Int. Cl.⁷ .................................................. A61C 3/06
(52) U.S. Cl. ........................................ 433/125; 433/104
(58) Field of Search .................................. 433/104, 125

(56) References Cited

U.S. PATENT DOCUMENTS

| | | | | |
|---|---|---|---|---|
| 3,727,313 A | * | 4/1973 | Graham | |
| 5,028,233 A | * | 7/1991 | Witherby | 433/125 |
| 5,642,995 A | * | 7/1997 | Bailey | 433/116 |
| 5,683,247 A | * | 11/1997 | Bailey | 433/104 |
| 5,911,577 A | * | 6/1999 | Henrikson | 433/125 |
| 6,053,732 A | * | 4/2000 | Sale | 433/125 |

* cited by examiner

Primary Examiner—John J. Wilson
(74) Attorney, Agent, or Firm—Polster, Lieder, Woodruff & Lucchesi

(57) ABSTRACT

A dental prophylaxis angle is provided having a body having a sleeve sized for fitting the nose of a dental handpiece, a drive part comprising a drive shaft extending into the sleeve and a drive member on the drive shaft. A driven part comprising a driven part shaft. The drive and driven parts has axes of rotation which are at substantial angles to each other. The drive part shaft is sized for gripping by a gripping mechanism in the handpiece. The drive member has a forward surface and a post extending from its forward surface. The drive part post is sized to limit end play of the drive part. Additionally, the drive part post has a shallow cavity formed in a forward surface thereof to reduce the contact area of the post with the driven part shaft, and to provide a reservoir for lubricant in the angle.

14 Claims, 3 Drawing Sheets

LUBRICATED DISPOSABLE PROPHYLAXIS ANGLE

CROSS-REFERENCE TO RELATED APPLICATIONS

Not Applicable

STATEMENT REGARDING FEDERALLY SPONSORED RESEARCH OR DEVELOPMENT

Not Applicable.

BACKGROUND OF THE INVENTION

This invention relates to dental prophylaxis angles. It has particular, although not exclusive, application to disposable dental prophylaxis angles.

Commercial embodiments of the disposable dental prophylaxis angles disclosed in Bailey, U.S. Pat. No. 5,328,369, which is incorporated herein by reference, and particularly the embodiments of FIGS. 1–5 and 7–8 of the noted Bailey patent, have been successfully sold by Young Dental Manufacturing Company of Earth City, Mo. for several years. Until the present invention, these angles have included the finger 53 on the cap and the groove 55 in the drive gear shaft for the purpose of controlling end play (excessive forward movement) of the drive shaft.

Other approaches to controlling end play of the drive shaft have been used. Thiedemann et al., U.S. Pat. No. 1,534,817, Graham, U.S. Pat. No. 3,727,313, and Warden et al., U.S. Pat. No. 4,266,933 have allowed the forward end of the drive gear to abut the shaft of the driven gear in order to limit end play. Kraenzle, U.S. Pat. No. 6,203,322, sizes a portion of the shaft of his driven gear for continuous engagement by a flat surface at the forward end of the drive shaft over a substantial area of the flat surface to limit the forward movement of the drive shaft. Commercial devices made in accordance with Graham, U.S. Pat. No. 3,727,313 include a short post, with a central opening extending deeply into the drive shaft, at the forward end of the drive gear.

All of these modified angles suffer from requiring a large area of contact between the drive gear or extension post and the shaft of the driven gear. This large contact area increases friction and makes lubricating the moving parts more difficult.

BRIEF SUMMARY OF THE INVENTION

Briefly stated, a dental prophylaxis angle of the present invention includes a body having a sleeve, a neck at the end of the sleeve, and a head formation at the end of the neck. A chamber is formed in the head formation and a passage extends through the neck and sleeve and is in communication with the head formation chamber. The sleeve is sized to fit the nose of a dental handpiece.

The dental angle includes a drive part having a drive shaft which extends through the neck and sleeve passage, a drive member near the forward end of the drive shaft, and a post extending from the forward surface of the drive member. The drive part shaft has an axis of rotation and is sized for gripping by a gripping mechanism in the handpiece.

The post has a cavity formed in a forward surface thereof. The cavity can be filled with a lubricant. The drive part post cavity is defined in part by a peripheral wall of the post. The cavity can have a generally concave surface. Alternatively, the cavity can be defined by a generally cylindrical wall and a bottom surface. Preferably, the drive part post has a height approximately equal about 5% to about 30% of the height of the drive gear (from the back surface of the drive gear to the forward surface of the drive gear).

The dental angle also includes a driven part which is received in the head formation chamber. The driven part includes a driven part shaft, a driven member, and a post to which a dental tool can be mounted. The driven member engages the drive member, such that the driven part is rotated by rotation of the drive part. The driven part has an axis of rotation at a substantial angle to the axis of rotation of the drive part.

The neck ends in a shoulder, and the drive member is sized to limit rearward movement of the drive shaft. Additionally, the drive part post is sized to limit end play of the drive part.

The driven part post has a length such that thrust loads are passed through the driven part shaft and borne by the angle body, rather than by the angle gears. To accomplish this, the length of the driven part shaft is about 11% to about 15% greater than the drive gear diameter.

Preferably, the drive part and the driven part are molded of plastic.

BRIEF DESCRIPTION OF THE SEVERAL VIEWS OF THE DRAWINGS

Corresponding reference numerals will be used throughout the several figures of the drawings.

DETAILED DESCRIPTION OF THE INVENTION

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention.

Figure 1:
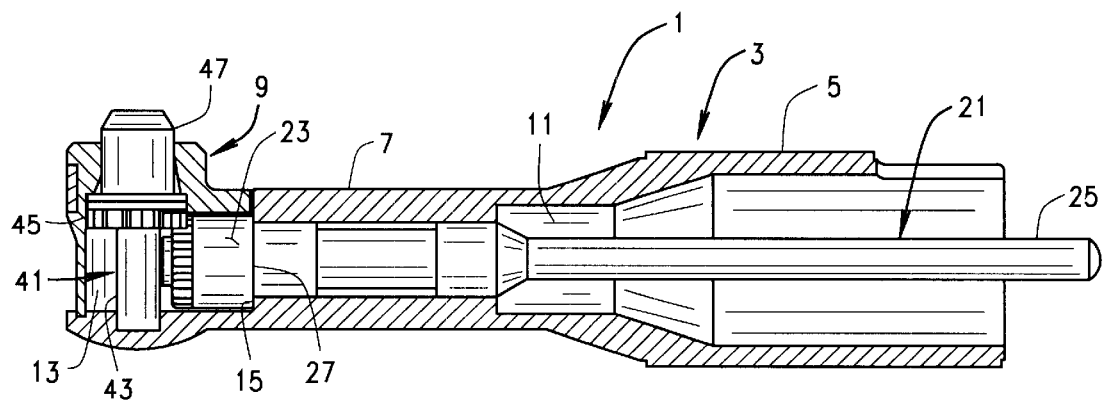
FIG. 1 is a cross-sectional view of a prophylaxis angle of the present invention.
Figure 2:
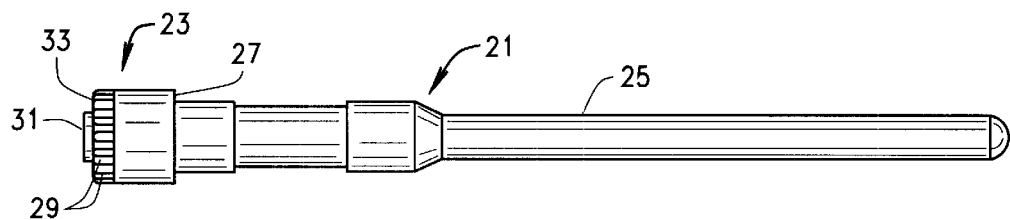
FIG. 2 is a side elevational view of a drive part having a drive shaft and drive member or gear.
Figure 3:
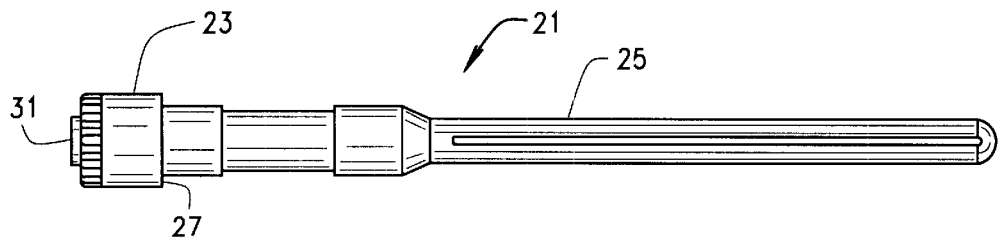
FIG. 3 is a view of the drive part rotated 90° relative to the view of FIG. 2.
Figure 4:
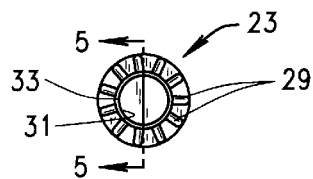
FIG. 4 is an end view of the drive member.

A prophylaxis (or dental) angle 1 of the present invention is shown generally in FIG. 1. The angle 1 includes a body 3 having a sleeve 5, a neck 7, and a head formation 9. The sleeve 5 is sized to be fit the nose of a dental handpiece, such as a Doriot. A passage 11 extends through the sleeve 5 and neck 7 and is in communication with a chamber 13 formed in the head formation 9. As seen in FIG. 1, a shoulder 15 is formed at the front of the neck 7 where the passage 11 intersects with the chamber 13.

The angle 1 is preferably formed as described in the above noted U.S. Pat. No. 5,328,369, which is incorporated herein by reference. Namely, the head formation 9 is formed essentially of two parts, a first part, which is formed integrally with the sleeve and neck, and a cap which closes the head first part. However, the head formation could be formed in many other ways as well, and the construction of the head formation does not constitute a part of the present invention. For example, the head formation could be formed in a clam shell formation, as shown and described in Kraenzle, U.S. Pat. No. 6,203,322. Alternatively, the head formation could be formed as a one-piece element which is secured to the neck.

Figure 5:
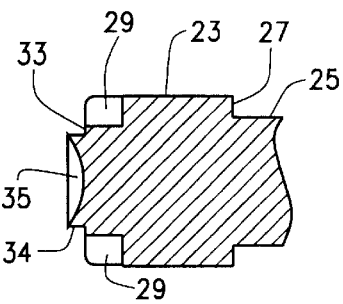
FIG. 5 is an enlarged cross-sectional view of the drive part taken along line 5—5 of FIG. 4 showing the cavity in the end post of the drive part.

A one-piece molded drive part 21 is received in the angle. The drive part includes a drive gear 23 near one end of a drive gear shaft 25. The shaft 25 is sized to be gripped by the gripping mechanism of a handpiece. The drive gear 23 is larger in diameter than the drive shaft 25 at the junction between the two, and hence, the drive part 21 includes a shoulder 27 at the back surface of the drive gear 23. The angle 1 is preferably formed such that the drive part is inserted into the passage 11 rear end first. The drive part 21 is inserted into the passage 11 until the shoulder or back surface 27 of the gear 23 abuts the neck shoulder 15. Hence, the drive gear 23 extends into the chamber 13 of the head formation 9. Drive gear teeth 29 are formed at the forward end of the drive gear 23, and a post 31 extends from the forward surface 33 of the drive gear 23. As seen in FIG. 5, the post 31 has a cavity 35 in the front surface of the post, the front surface of the post defining, in this embodiment, the front surface of the drive part. The cavity 35 is a shallow cavity; that is, the cavity is wider than it is deep. Preferably, the cavity is bounded by the outer wall 34 of the post and is concave. The concavity of the front surface of the post may be of any shape, although a particularly convenient shape is for it to be sloped inward from the outer wall. Preferably, the diameter of the cavity at the forward end of the post is greater than 50% of the diameter of the post.

Figure 6:
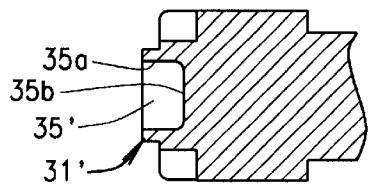
FIG. 6 is a cross-sectional view of an alternative embodiment of the post of the drive part.

An alternate embodiment of the drive part post 31' is shown in FIG. 6. In this embodiment, the cavity 35' is deeper, forming more of a bowl. Rather than being defined by a sloped or concave surfaces, the cavity 35' is defined by a generally cylindrical side wall 35a and a generally flat bottom 35b.

Figure 7:
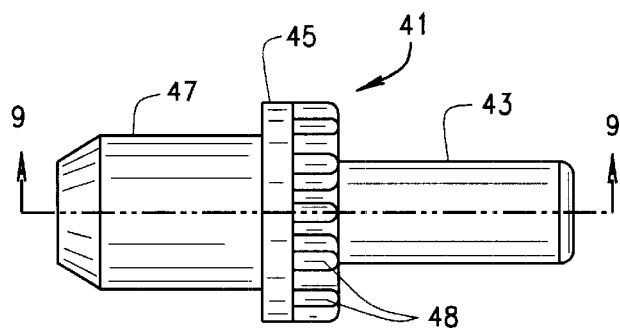
FIG. 7 is a side elevational view of a driven part of the prophylaxis angle.
Figure 8:
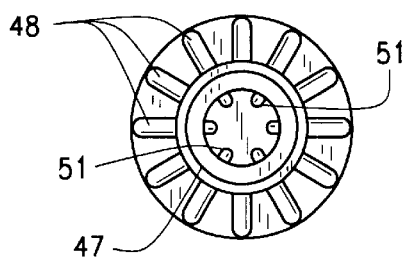
FIG. 8 is an end view of the driven part.
Figure 9:
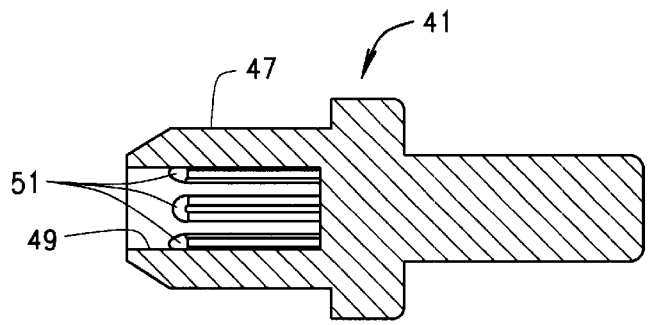
FIG. 9 is a cross-sectional view of the driven part.

A one-piece molded driven part 41 (shown in detail in FIGS. 7–9) is received in the head formation chamber 13. The driven part 41 includes a shaft 43, a driven gear 45 at the end of the shaft 43, and a post 47. The driven gear 45 has teeth 48. The post 47 is adapted to receive a tool, such as a prophylaxis cup, brush, etc. Illustratively, the driven part post 47 includes a bore 49 with splines 51. The tool includes a threaded shaft, and the splines 51 and shaft are sized so that the shaft threadedly engages the splines 51 when the tool is secured to the post 47.

When the drive and driven parts are placed in the angle 1, the drive gear teeth and driven gear teeth are in meshing contact, such that the driven gear 45, and hence the post 47 and tool will rotate as the drive gear 23 rotates.

The driven gear shaft 43 is preferably sized such that thrust loads applied to the angle during use will pass through to the bottom of the head formation. Thus, the thrust loads will be borne by the angle body, rather than the gears. Hence, high thrust loads will not cause the gears to "bottom out" or "over-mesh," that is, the drive and driven gears will not be forced to mesh to such an extent that the teeth of the respective gears are urged into the clearance of the opposing gear, which would potentially result in seizing-up of the gears.

The drive part post 31 (or 31') is sized to reduce end play in the drive part, again, to reduce the possibility of the drive and driven gears from bottoming out should the drive part be pushed forward against the driven part. Thus, the drive part post 31 (or 31') is sized slightly less than the distance between the end surface 33 of the drive gear 23 and the driven gear shaft 43. It has been found that in normal testing conditions, the drive part post 31 (or 31') is sized such that, during operation of the angle, the drive part post 31 (or 31') does not generally contact the driven gear shaft 43. Contact between the drive part post and the drive part shaft will occur, however, when the angle is subject to extreme loading conditions.

The end surface of the post (or the drive part) is shown, for example, in FIG. 6 to be flat. However, this end surface, which defines a contact surface if and when drive part contacts the driven part shaft, can be any desired shape. For example, the end surface can be curved convexly or concavely. Additionally, the surface can slope or curve radially inwardly or outwardly.

In a preferred construction of the angle 1, and the drive and driven parts 21 and 41, the drive gear has a diameter of about 0.19" and a length between its back surface 27 and the forward surface of the post 31 (or 31') of about 0.185"; the drive part post 31 (or 31') has a height from the drive gear surface 33 to the forward end of the post 31 (or 31') of about 0.018" and a diameter of about 0.1"; the drive gear teeth 29 have an axial depth of about 0.043". The post cavity 35 has a depth of about 0.003". The second embodiment of post cavity 35' has a depth of about 0.02". On the driven part 41, the shaft 43 has a length of about 0.215" and a diameter of about 0.1"; the driven gear has a diameter of about 0.2"; and the drive teeth have an axial height of about 0.043".

The construction of the drive part post 31 (or 31') reduces contact of the post 31 with the driven part shaft 43 if (or when) pressures are exerted on the angle during use, which would cause the drive part post 31 to engage the driven part shaft 43. As can be appreciated, if the drive part post were solid (or had a flat end surface) there would be a substantial amount of surface engagement of the drive part post with the driven part shaft. It has been found that such engagement hinders operation of the angle 1. The cavity 35 (or 35') reduces the contact between the drive part post 31 (or 31') and the driven part shaft 43 to two points or small areas of contact. Thus, the upstanding periphery of the cavity is preferably relatively narrow to form an insubstantial contact surface with the driven part shaft. That is, in cross-section the potentially contacting surface of the drive part post is preferably less than twenty percent of the total width of the post, and more preferably, the width of the potentially contacting surface is less than ten percent of the total width of the post.

The cavity 35 (or 35') also provides a small reservoir which can receive lubricant. A preferred lubricant is a semi-solid gel, calcium soap type grease available from Century Lubricants—FUCHS of Kansas City, Kans. under the product code FMG 387. Other lubricants could be used. Hence, the angle can be easily lubricated during assembly of the angle and a controlled quantity of lubricant can be stored in the cavity for release onto the driven gear as the angle 1 is used. The cavity 35 (or 35') is simply filled with lubricant prior to insertion of the drive part 21 into the angle body 3.

During operation of the angle, the lubricant will lubricate the points of contact between the drive part post 31 and the driven part shaft 43 (if and when contact occurs). Additionally, lubricant will, to some degree, will be distributed throughout the chamber 13, thereby providing lubrication for the teeth of the drive and driven gears. This lubrication will facilitate smoother operation of the angle.

Figure 10:
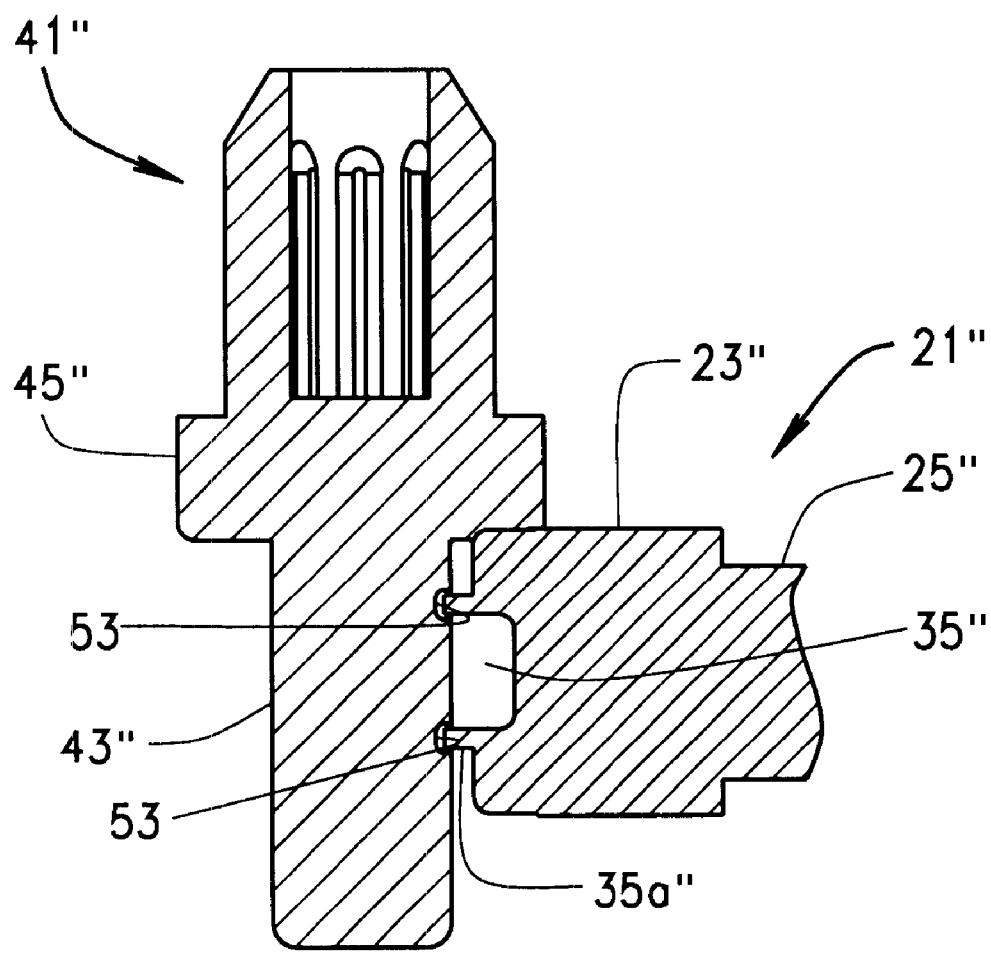
FIG. 10 is a cross-sectional view of another alternative embodiment for the drive and driven parts.

Another embodiment of the drive part 21" and the driven part 41" is shown in FIG. 10. In this embodiment, the drive part 21" includes a drive member 23" near the end of a drive shaft 25". A cavity 35" is defined by an annular wall 35a" extending from the end of the drive member. As shown, the cavity 35" is deeper than the wall 35a". The driven part 41" includes a driven member 45" at an end of a driven shaft 43". The driven shaft 43" has a pair of circumferential grooves 53 formed therein. The grooves 53 are spaced apart a distance equal to the diameter of the cavity 35", and are positioned on the shaft 43" to be aligned with the drive part wall 35a" when the drive member and driven member are in meshing contact. Thus, if and when the drive part contacts the driven part, the annular wall 35a" will engage the groove 53 of the driven part 41. When the driven part wall 35a" does engage the groove 53, the wall 51a" will reduce the play of the drive part 41" in the chamber 13, and help distribute the thrust loads rearwardly into the body neck, where the thrust loads can be absorbed by the neck structure.

As various changes could be made in the above constructions without departing from the scope of the invention, it is intended that all matter contained in the above description or shown in the accompanying drawings shall be interpreted as illustrative and not in a limiting sense. The size and shape of the cavity may be varied, although it is preferred that the cavity be relatively shallow, that is wider than it is deep. Although the post and cavity have particular utility in a disposable prophylaxis angle in which the drive part is inserted from the front, it can be used in other types of prophylaxis angles, for example, metal prophylaxis angles. Depending on the shape of the drive gear or member, the post can be eliminated, and the cavity can be formed in the forward surface of the drive member. In the embodiment of FIG. 10, if the drive part shaft were to be tapered, such that its diameter is greater near the driven member than at the bottom of the driven shaft, the groove spaced farthest from the driven part shaft could be eliminated. These examples are merely illustrative.

What is claimed is:

1. A dental prophylaxis angle comprising:
    a body having a sleeve, a neck at the end of the sleeve, and a head formation at the end of the neck; a chamber in the head formation; a passage extending through the neck and sleeve and in communication with the head formation chamber; and a shoulder at the forward end of the neck;
    a drive part comprising a drive shaft which extends through the neck and sleeve passage, a drive member near a forward end of the drive shaft and having a forward surface and a back surface; and a post extending from the forward surface of the drive member, the post including a cavity formed in a forward surface thereof; said cavity being wider than it is deep and having a diameter which is more than fifty percent of the total width of the post;
    a driven part received in the head formation chamber, the driven part comprising a driven part shaft, a driven member, and a post to which a dental tool can be mounted; the driven member engaging the drive member, such that the driven part is rotated by rotation of the drive part;
    the neck shoulder and drive member being sized to limit rearward movement of the drive shaft, and the drive part post being sized to limit end play of the drive part.

2. The dental angle of claim 1 including lubricant, the lubricant being received in the cavity of the drive part post.

3. The dental angle of claim 1 wherein the cavity of the drive part post is defined in part by a peripheral wall of the post.

4. The dental angle of claim 1 wherein the cavity of the drive part post is defined by a generally cylindrical wall and a bottom surface.

5. The dental angle of claim 1 wherein the drive part gear has a height from its back surface to its forward surface; and the post has a height from the drive gear forward surface to the forward surface of the post; the post height being equal to about 5% to about 30% of the drive gear height.

6. The dental angle of claim 1 wherein the driven part post has a length such that thrust loads are passed through the driven part shaft and borne by the angle body, rather than by the angle gears.

7. The dental angle of claim 1 wherein the drive part and the driven part are molded of plastic.

8. A dental prophylaxis angle comprising:
    a body having a sleeve, a neck at the end of the sleeve, and a head formation at the end of the neck; a chamber in the head formation; a passage extending through the neck and sleeve and in communication with the head formation chamber; and a shoulder at the forward end of the neck;
    a drive part comprising a drive shaft which extends through the neck and sleeve passage, a drive member near a forward end of the drive shaft and having a forward surface and a back surface; and a post extending from the forward surface of the drive member, the post including a cavity formed in a forward surface thereof; said drive part post defining an annular wall surrounding said cavity;
    a driven part received in the head formation chamber, the driven part comprising a driven part shaft, a driven member, and a post to which a dental tool can be mounted; the driven member engaging the drive member, such that the driven part is rotated by rotation of the drive part; said driven part including a circumferential groove on said driven part shaft; said groove being positioned on said shaft to be aligned with said annular wall;
    the neck shoulder and drive member being sized to limit rearward movement of the drive shaft, and the drive part post being sized to limit end play of the drive part.

9. The dental angle of claim 8 wherein said drive part includes a second groove on said drive part shaft; said second groove being spaced axially from said first groove, said grooves being positioned to be aligned with said annular wall to receive said annular wall upon contact of said drive part post with said driven part shaft.

10. A dental prophylaxis angle comprising:
    a body having a sleeve sized for fitting the nose of a dental handpiece,
    a drive part comprising a drive shaft extending into the sleeve, the shaft having an axis of rotation and being sized for gripping by a gripping mechanism in the handpiece, a drive member on the drive shaft, the drive member having a forward surface; and a post extending from the forward surface of the drive member, the post including a shallow cavity formed in a forward surface thereof; said cavity being wider than it is deep and having a diameter which is more than fifty percent of the total width of the post;

a driven part comprising a driven part shaft having an axis of rotation at a substantial angle to the axis of rotation of the drive part, a driven member, and a post to which a dental tool can be mounted; the driven member engaging the drive member, such that the driven part is rotated by rotation of the drive part;

the drive part post being sized to limit end play of the drive part.

11. The dental angle of claim 10 including a lubricant received in the cavity.

12. The dental angle of claim 10 wherein the angle is a disposable angle formed of molded plastic parts.

13. A dental prophylaxis angle comprising:

a body having a sleeve sized for fitting the nose of a dental handpiece, a drive part comprising a drive shaft extending into the sleeve, the shaft having an axis of rotation and being sized for gripping by a gripping mechanism in the handpiece, a drive member on the drive shaft; the drive part having a forward surface; and a lubricating reservoir formed in a forward surface thereof for holding a quantity of lubricant; said reservoir being wider than it is deep and having a diameter which is more than fifty percent of the total width of the post;

a driven part comprising a driven part shaft having an axis of rotation at a substantial angle to the axis of rotation of the drive part, a driven member, and a post to which a dental tool can be mounted; the driven member engaging the drive member, such that the driven part is rotated by rotation of the drive part;

the drive part forward surface and the driven part shaft being sized to limit end play of the drive part.

14. A dental prophylaxis angle comprising:

a body having a sleeve sized for fitting the nose of a dental handpiece, a drive part comprising a drive shaft extending into the sleeve, the shaft having an axis of rotation and being sized for gripping by a gripping mechanism in the handpiece, a drive member on the drive shaft; the drive part having a forward surface; and a shallow lubricant reservoir formed in a forward surface thereof which receives a lubricant; said reservoir being wider than it is deep and having a diameter which is more than fifty percent of the total width of the post;

a driven part comprising a driven part shaft having an axis of rotation at a substantial angle to the axis of rotation of the drive part, a driven member, and a post to which a dental tool can be mounted; the driven member engaging the drive member, such that the driven part is rotated by rotation of the drive part.

* * * * *